United States Patent [19]

Bertolini et al.

[11] Patent Number: 5,424,304
[45] Date of Patent: Jun. 13, 1995

[54] 17-ARYL-SUBSTITUTED STEROIDAL COMPOUNDS ACTIVE ON THE CARDIOVASCULAR SYSTEM

[76] Inventors: Giorgio Bertolini, Via A. Costa, 37, 20099 Sesto S. Giovanni (Milan); Cesare Casagrande, Via Campogallo, 21/67, 20020 Arese (Milan); Gabriele Norcini, Via S. G. Bosco, 39, 21019 Maddalena Somma Lombardo (Varese); Francesco Santangelo, Via Don Gnocchi, 33, 20148 Milan, all of Italy

[21] Appl. No.: 4,410

[22] Filed: Jan. 15, 1993

[30] Foreign Application Priority Data

Jan. 16, 1992 [IT] Italy .................. MI92A0076

[51] Int. Cl.$^6$ .................. C07J 1/00; C07J 43/00
[52] U.S. Cl. .................. 514/176; 514/182; 536/5; 536/6; 540/108; 540/113; 552/612; 552/616; 552/633; 552/636; 552/641
[58] Field of Search ............... 536/6, 5; 540/108, 113; 552/612, 616, 633, 636, 641; 514/176, 182

[56] References Cited

PUBLICATIONS

K. R. H. Repke, *TIPS*–(Jul. 1985), Elsevier Science Publishers, BV Amsterdam, pp. 275,278, "New Developments in Cardia Glycoside".
Uttam K. Pati et al, Heterocycles, 29 (7), pp. 1275–1282 (1989) "Synthesis of 5β-Androstan-17β-(1'Oxocyclohex-1'-EN-3'-YL) . . . ".
J. C. Beloeil et al, Tetrahedron 39 (23), pp. 3937–3941 (1983) "Synthetic Studies in the Cardenolide Series—II, . . . ".
O. Mitsunobu, Synthesis, 1, (1981), "The Use of Diethyl Azzodicarboxylate and Triphenylphosphine in Synthesis and . . . ".
Richard R. Schmidt, Agnew. Chem. Int. Ed. Engl., 25, (1986), pp. 212–235, "New Methods for the synthesis of Glycosides . . . ".
Hans Paulsen, Agnew. Chem. Int. Ed. Engl., 21, (1982) pp. 155–173, "Advances in Selective Chemical Synthesis of . . . ".
Karel Wiesner et al, Helv. Chim. Acta, 68, (1985), pp. 300–314 "On Cardioactive Steroids. XVI. Stereoselective β-Glycosylation."
F. Noel et al, *Biochemical Pharmacology*, 40 (12), pp. 2611–2616 (1990), "A Comparision of the Affinities of Rate (Na+ +K+)-. . . ".

*Primary Examiner*—Johann Richter
*Assistant Examiner*—Kimberly J. Kestler
*Attorney, Agent, or Firm*—Stevens, Davis, Miller & Mosher

[57] ABSTRACT

Cardioactive steroidal compounds of the formula I

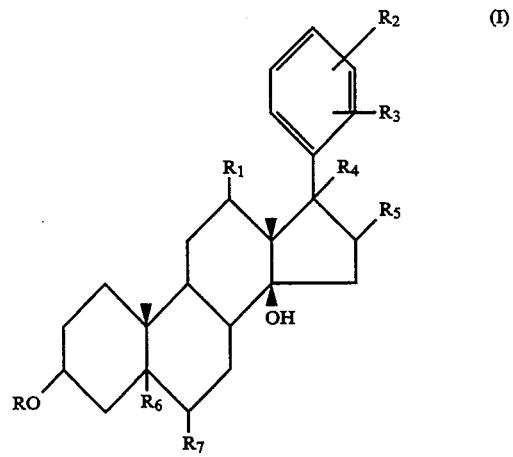

wherein R, $R_1$, $R_2$, $R_3$, $R_4$, $R_5$, $R_6$ and $R_7$ have the meanings shown in the description, and pharmaceutical compositions containing them.

12 Claims, No Drawings

17-ARYL-SUBSTITUTED STEROIDAL COMPOUNDS ACTIVE ON THE CARDIOVASCULAR SYSTEM

The present invention relates to steroidal compounds active on the cardiovascular system.

More particularly, the present invention relates to cardioactive steroidal compounds having an aromatic nucleus at the 17-position and the pharmaceutical composition containig them.

Naturally occurring steroidal compounds endowed with digitalis-like cardiotonic activity have an unsaturated lactone ring at the 17-position.

Studies on molecular modifications have shown that the natural lactone ring can be replaced by other groups while maintaining, to a certain degree, the digitalis-like activity (see, for example, K. R. H. Repke, TIPS—July 1985 —Elsevier Science Publishers B. V. Amsterdam, pp. 275–278), Among the most important examples, described in the literature, of groups replacing the natural ring there are the heterocyclic structures such as lactone isomers, furans, pyridazine, pyrrolidinones and open structures.

As far as we know, the substitution with an aryl group at the 17-position to obtain a cardioactive steroidal compound has never been described.

In this connection, it is very important to note that steroidal compounds substituted at the 17-position with a 3-methoxyphenyl group have been described as intermediates useful for the synthesis of cardioactive steroidal glycosides having a cyclohexenone ring in the 17-position (Pati Uttam K. et al., Heterocycles, 29(7), pp. 1275–1282, (1989)).

Now, we have surprisingly found that the unsaturated lactone ring at the 17-position of naturally occurring cardioactive steroidal compounds can be replaced by an aryl group without loss of the digitalis-like activity.

It is therefore an object of the present invention to provide the compounds of the formula I

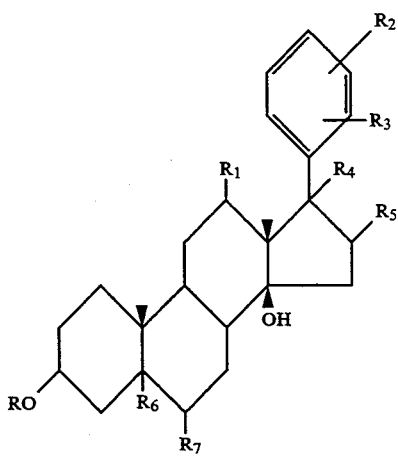

(I)

wherein

R is hydrogen, a glycidic group or an aminoalkyl group of the formula $-(CH_2)_n-NR_8R_9$, wherein n is 2 or 3, and where $R_8$ and $R_9$, which may be the same or different, are straight or branched $C_1-C_4$ alkyl groups, or form, together with the nitrogen atom to which they are linked, a heterocycle having 5, 6 or 7 members, which may include one or two heteroatoms selected from oxygen and nitrogen, and may optionally be substituted with a straight or branched $C_1-C_4$ alkyl group;

$R_1$ is hydrogen or hydroxy;

$R_2$ and $R_3$, which may be the same or different, are hydrogen, fluorine, chlorine, bromine, iodine, a straight or branched $C_1-C_4$ alkyl, a straight or branched $C_1-C_4$ polyhalogenated alkyl, OH, $OR_{10}$, $OCOR_{10}$, $NH_2$, $NHR_{10}$, $N(R_{10})_2$, $NHCOR_{10}$, SH, $S(O)_mR_{10}$, $NHSO_2R_{10}$, CHO, $COOR_{10}$, $CON(R_{10})_2$ or CN where $R_{10}$ is a straight or branched $C_1-C_4$ alkyl, a straight or branched $C_1-C_4$ polyhalogenated alkyl or an aryl and m is zero, 1 or 2;

or $R_2$ and $R_3$ together form a $C_3-C_4$ alkylydene, which may have one or two unsaturated bonds, or they may form a $-O-(CH_2)_p-O-$ group, where p is 1 or 2;

$R_4$ is hydrogen;

$R_5$ is hydrogen or hydroxy;

or $R_4$ and $R_5$ together form a covalent bond;

$R_6$ and $R_7$ are hydrogen or together form a covalent bond; and the substituents in the 10-, 13-, and 14-position have beta configuration, provided, however, that when R, $R_1$, $R_4$, $R_5$, $R_6$ and $R_7$ and either $R_2$ or $R_3$ are hydrogen atom, then the remaining of $R_2$ and $R_3$ is not a 3-methoxy group.

The compounds of formula I according to this invention are useful in the therapy of pathologies of the cardiovascular system and, particularly, in the treatment of heart failure and hypertension.

Specific examples of glycidic groups included in the meaning of R are the monosaccharides such as D-glucose, D-lissose, D-xylose, 2-deoxy-D-glucose, D-allomethylose, D-tevetose, L-tevetose, L-talomethylose, D-gulomethylose, D-glucomethylose, L-rhamnose, L-acofriose, D-fucose, L-fucose, D-digitalose, L-acovenose, D-digitoxose, D-cymarose, D-boivinose, D-sarmentose, L-oleandrose, D-oleandrose, D-diginose or the di- and trisaccharides consisting, respectively, of two or three of the above mentioned monosaccharides.

Examples of compounds of formula I are as follows

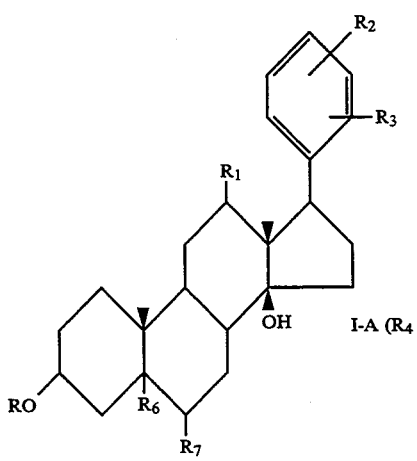

I-A ($R_4 = R_5 = H$)

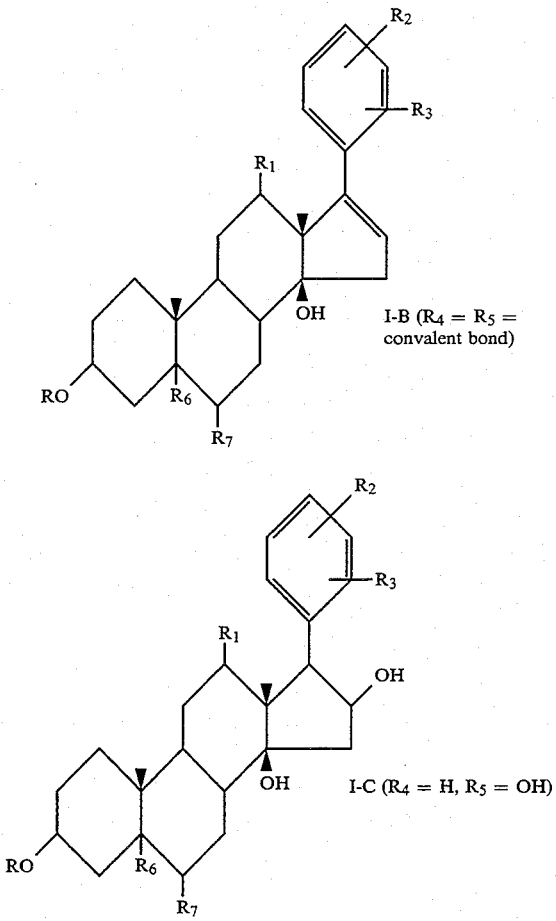

I-B ($R_4 = R_5$ = convalent bond)

I-C ($R_4 = H$, $R_5 = OH$)

wherein R, $R_1$, $R_2$, $R_3$, $R_6$ and $R_7$ have the above mentioned meanings.

Unless otherwise stated, the term straight or branched $C_1$–$C_4$ alkyl group refers to groups such as methyl, ethyl, n-propyl, isopropyl, n-butyl, sec-butyl and tert-butyl; the term straight or branched $C_1$–$C_4$ polyhalogenated alkyl group refers to groups such as trifluoromethyl, trichloromethyl, hexafluoroethyl, fluoromethyl and difluoromethyl; the term aryl refers to optionally substituted rings such as phenyl and naphthyl; the term heterocycle having 5, 6 or 7 members refers to groups such as pyrrolidine, imidazolidine, pyrazolidine, piperidine, piperazine, morpholine, tetrahydropyrimidine, tetrahydroisoxazole, tetrahydroxazole and tetrahydroazepine.

Preferred compounds of formula I are the compounds wherein $R_2$ and $R_3$, which may be the same or different, are hydrogen, fluorine, chlorine, bromine, iodine, methyl, ethyl, trifluoromethyl, OH, methoxy, CN, $NH_2$, $NHR_{10}$ or $N(R_{10})_2$, or $R_2$ and $R_3$ together form a $C_4$ alkylydene having one or two unsaturated bonds; $R_6$ and $R_7$ are hydrogen.

Most preferred compounds are those compounds of the formula I wherein $R_1$, $R_6$ and $R_7$ are hydrogen; $R_2$ and $R_3$, which may be the same or different, are hydrogen, fluorine, methyl, methoxy or trifluoromethyl, or $R_2$ and $R_3$ together form a $C_4$ alkylydene having two unsaturated bonds.

The process for the preparation of the compounds of formula I is given by the following scheme 1.

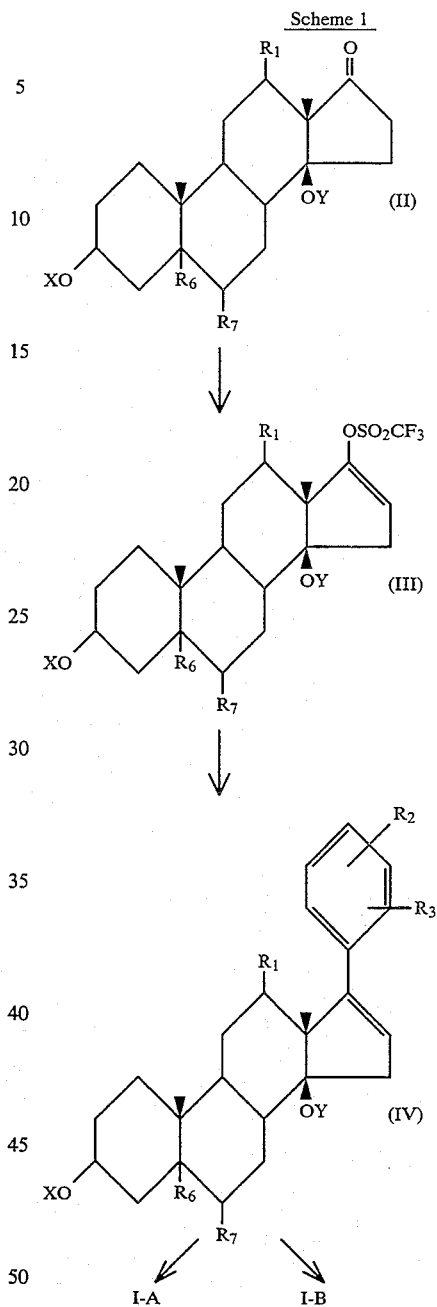

Scheme 1 wherein
$R_1$, $R_2$, $R_3$, $R_6$ and $R_7$ are as described above;
X is the same as R or is a protective group or a suitably protected glycidic group;
Y is hydrogen or a protective group.

The compounds of formula II are well known or can be easily prepared according to conventional techniques, such as that described by Beloeil et al. in Tetrahedron 39(23), pp. 3937–3941, (1983), or can be prepared from digitoxygenin or digoxygenin.

Preferably, there are used the compounds of formula II where X and Y are protective groups such as benzyl, acetyl, trimethylsilyl and ethoxymethoxy or, in the case of the X group, the hydroxy groups of the glycidic group are suitably protected as ethoxymethoxy groups.

Similarly, in the preparation of the compounds of formula I where $R_1=OH$, it is preferred to use a compound of formula II where the second hydroxy group at the 12 position is protected.

The starting compounds of formula II are treated with trifluoromethanesulfonic anhydride in the presence of organic or inorganic bases, or, alternatively, firstly with bases such as butyl lithium, sodium hydride, lithium diisopropylamine and then with N-phenyltrifluoromethanesulfonimide, to give the compounds of formula III. The subsequent step involves the substitution at the 17-position with an optionally substituted phenyl group, by reacting the compounds of formula III with organometallic compounds of the formula

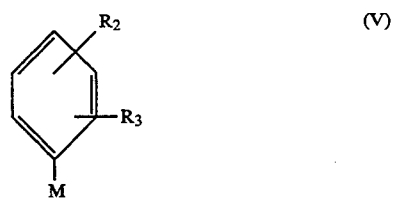

(V)

where $R_2$ and $R_3$ are as described above and M is Cu, $(C_4H_9)_3Sn$, $ZnX_1$, $MgX_1$ or $B(OH)_2$, where $X_1$ is a halogen atom; optionally in the presence of palladium- or nickel-based catalysts and alkaline metal salts such as lithium chloride and sodium carbonate.

It is evident that the substituting groups $R_2$ and $R_3$ can also be present in the organometallic compound V, optionally in a masked or protected form.

It is up to the person skilled in the art to judge whether or not to use said substituting groups in the masked or protected form in view of the selected reaction conditions.

However, in practice, possible masked or protected forms of the substituting groups $R_2$ and $R_3$ are, for example, acetals or thioacetals of the aldehyde group, or precursors of other functional groups.

Thus, for example, when condensing the compound of formula III with the organometallic compound V, on the phenyl ring there can be present optionally protected OH, $NH_2$ or SH groups, which can be then transformed, in one of the subsequent steps of the process, into the corresponding groups $OR_{10}$, $OCOR_{10}$, $N(R_{10})_2$ $NHCOR_{10}$, $NHSO_2R_{10}$, $S(O)_mR_{10}$ according to conventional techniques of alkylation, acylation or oxidation.

Upon completing the condensation reaction with the compound V, compound IV is obtained, which has an unsaturated bond at 16 and 17 while the hydroxyl functions on the steroid nucleus are optionally protected.

From compound IV, there are obtained
the compounds of formula I-A, by reduction of the 16-17 double bond and deprotection, when required, or
the compounds of formula I-B by mere deprotection of the hydroxyl groups.

Generally, the deprotection is performed by hydrogenation or hydrolysis.

Hydrogenation is preferably performed with hydrogen, in the presence of a suitable catalyst, such as palladium-on-charcoal, platinum oxide, platinum-on-charcoal, rhodium-on-alumina or $eta^4$-1,5-cyctooctadiene(-pyridine)(tricyclohexylphosphine)-iridium-(I)hexaflurophosphate ($[Ir(cod)py(Cy_3P)]PF_6$).

Obviously, for the case where the protective group is benzyl, hydrogenation of the 16-17 double bond causes simultaneous deprotection.

Similarly, hydrogenation also causes simultaneous reduction of the 5-6 double bond, if any.

The compounds of formula IV are also useful intermediates for the preparation of the compounds of formula I-C according to the process shown by the following scheme 2

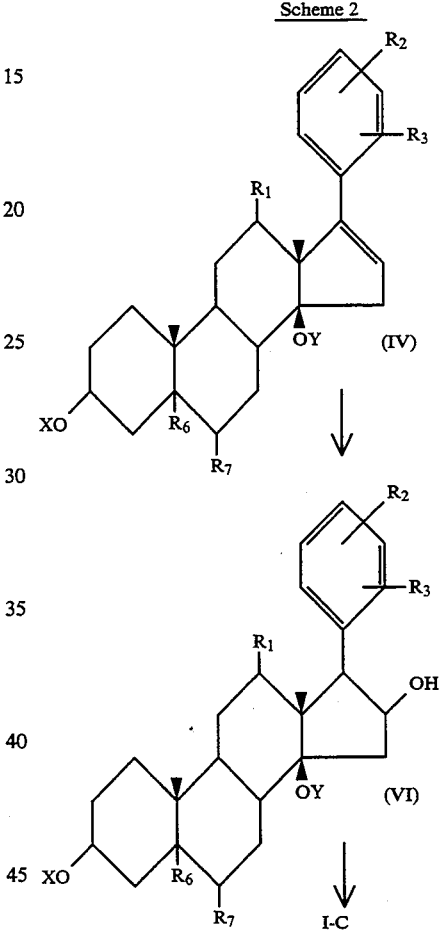

Scheme 2 where $R_1$, $R_2$, $R_3$, $R_6$, $R_7$, X and Y are as described above.

The compounds of formula VI, where the hydroxyl at the 16-position is alpha, are prepared by hydroboration and subsequent oxidation of the corresponding compounds of formula IV, according to conventional techniques.

The hydroxyl at the 16-position can be inverted to obtain the corresponding compound of formula VI, where the hydroxyl is beta, according to the method described by O. Mitsunobu in Synthesis, 1, (1981).

The subsequent deprotection, according to the above mentioned techniques, yields the compounds of the formula I-C.

Alternatively, the compounds of formula VI can be utilized as intermediates for the preparation of the compounds of formula I-A in the process shown in the following scheme 3.

Scheme 3

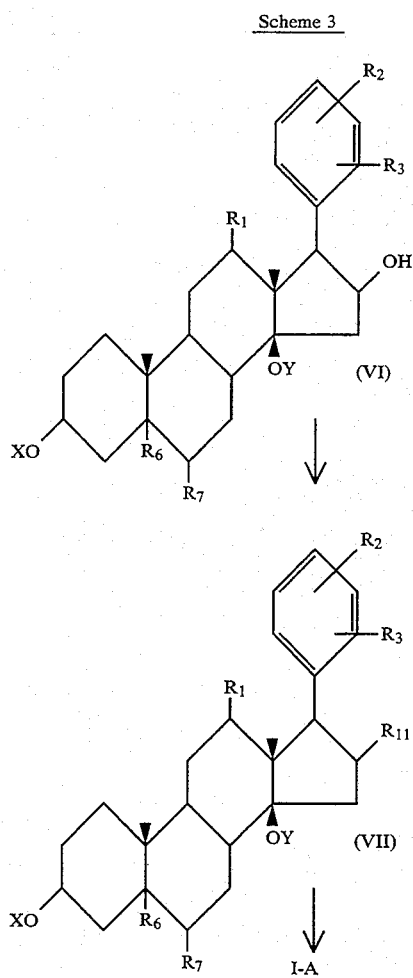

wherein $R_1$, $R_2$, $R_3$, $R_6$, $R_7$, X and Y are as described above and $R_{11}$ is trifluoromethanesulfonyloxy, mesyloxy or p.toluenesulfonyloxy, bromine or iodine.

The transformation of compound VI to the corresponding compound VII is performed according to conventional sulfonylation techniques with suitable reactive derivatives of sulfonic acids, optionally substituted.

The compounds of formula I-A are obtained by subsequent treatment of compound VII with hydrides, such as lithium boron hydride, sodium boron hydride, lithium and aluminium hydride, or tributyltin hydride.

Another alternative for the preparation of the compounds of formula I-A is shown in the following scheme 4.

Scheme 4

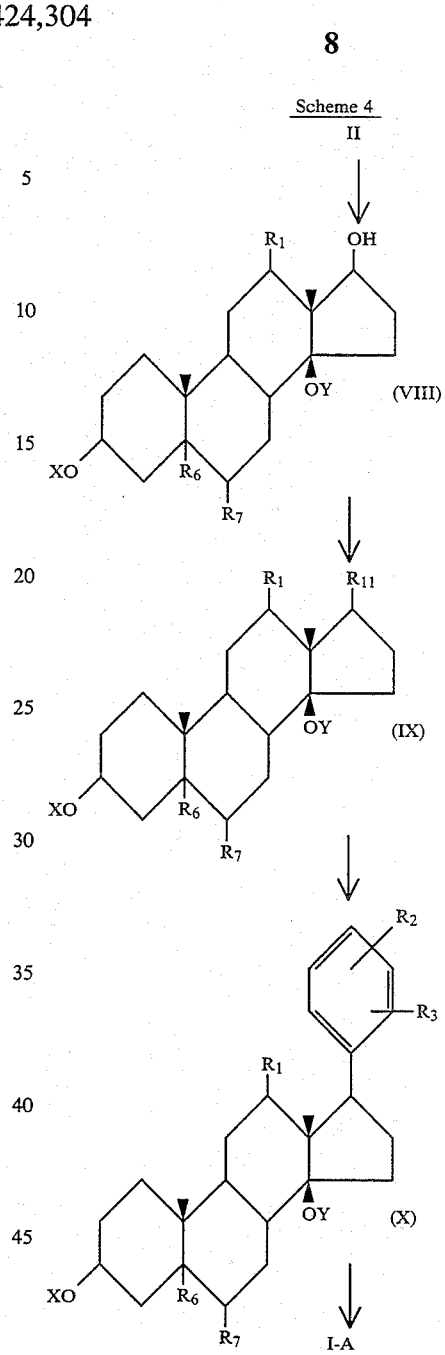

where $R_1$, $R_2$, $R_3$, $R_6$, $R_7$, X, Y and $R_{11}$ are as described above.

The compound of formula II is reduced, according to conventional techniques, with reducing agents such as sodium boron hydride, lithium aluminium hydride and lithium boron hydride. The subsequent transformation of the hydroxyl group at the 17-position is carried out as described above in the Scheme 3 for the preparation of compound VII.

The treatment of compound IX thus obtained with organometallic compounds of formula V where M=Cu gives the compounds of formula X, which by deprotection and glycosidation yields the compounds of formula I-A.

It is evident that, as already stated, depending on the compound of formula II used as the starting material in the above described processes, compounds of formula I, where R is a hydrogen atom, can be obtained by deprotection. From these, (formula I, R=H) the corresponding compounds of formula I, where R is a glycidic group, can be prepared with conventional glycosidation reactions.

Among the glycosidation methods reported in the literature, the following can be cited: Schmidt, Angew. Chem. Int. Ed. Engl., 25, (1986), 212; Paulsen, Angew. Chem. Int. Ed. Engl., 21, (1982), 155, and; Wiesner et al., Helv. Chim. Acta, 68, (1985), 300.

The compounds of formula I are useful in the therapy of pathologies of the cardiovascular system since they possess positive inotropic activity, sometimes associated with a vasodilatig activity, and thereby they exercise favourable effects, especially in the heart failure and hypertension.

The activity of the compounds of formula I has been evaluated with the binding test on the alpha$_1$ and alpha$_3$ isoforms of rat ($Na^+ + K^+$)-ATPase in rat kidney and rat brain, according to the method described by Noel F. et al. in Biochemical Pharmacology, 40(12), 2611–2616, (1990) (see Example 9).

The compounds of formula I interact at very low concentrations, as far as the alpha$_3$ isoforms are concerned. Moreover, their selectivity towards the alpha$_3$ isoforms, and as a consequence their therapeutic index, is higher in comparison to the naturally occurring cardioactive glycosides such as digoxin (see Example 9).

For practical therapeutic applications the compounds of formula I are formulated into pharmaceutical forms suitable for oral or parenteral administration.

In general, the therapeutic doses are of from 0.01 to 100 mg/day.

It is therefore a further object of the present invention to provide pharmaceutical compositions containing a therapeutically effective amount of a compound of formula I together with a pharmaceutical carrier.

The pharmaceutical compositions of the present invention are prepared according to conventional techniques.

The following examples are given to further illustrate the present invention.

EXAMPLE 1

3-beta-[[6-deoxy-2,4-di-(ethoxymethyl)-3-O-methyl-alpha-L-glucopyranosyl]oxy]-14-ethoxymethoxy-5-beta, 4beta-androst-16-en-17-yl-triflate To a solution of diisopropylamine (7.35 g; 72.6 mmoles) in dry tetrahydrofuran (90 ml), cooled to a temperature of from $-5°$ C. to $0°$ C., a solution of 1.6M n.butyl lithium in hexane (45.3 ml; 72.6 mmoles) is added slowly under nitrogen.

The reaction mixture is stirred for 15 minutes at the same temperature. The solution is then cooled to $-75°$ C. and a solution of 3beta-[[6-deoxy-2,4-di-(ethoxymethyl)-3-O-methyl-alpha-L-glucopyranosyl]oxy]-14-ethoxymethoxy-5beta,14beta-androstan-17-one (31 g; 48.4 mmoles) in dry tetrahydrofuran (90 ml) is added.

The reaction mixture is maintained under stirring at $-75°$ C. for 1 hour. Then, a solution of N-phenyltrifluoromethanesulfonimide (19 g; 53.2 mmoles) in dry tetrahydrofuran (90 ml) is added.

When the addition is over, the reaction mixture is heated to $0°$ C. and maintained under stirring at this temperature for 2 hours. The solvent is removed and the thus obtained crude product is purified by column chromatography on silica gel (230–400 mesh) (eluent, methylene chloride:ethyl acetate, concentration gradient of ethyl acetate from 2 to 15 %) to yield the desired compound in the form of an oil (31 g).

An analytical sample was crystallized from ethyl alcohol: water =1:1 (m.p. 42°–44° C.).

$^1$H-NMR (300 MHz, CDCl$_3$): delta (ppm): 0.95 (s, 3H); 1.07 (s, 3H); 1.18 (t, 3H); 1.20 (t, 3H); 1.22 (t, 3H); 1.23 (d, 3H); 1.00–2.00 (m, 17H); 2.56 (dd, 1H); 2.63 (dd, 1H); 3.12 (bt, 1H); 3.57 (s, 3H); 3.50–3.80 (m, 9H); 3.88 (bs, 1H); 4.67 (d, 1H); 4.75 (s, 2H); 4.77 (d, 1H); 4.79 (d, 1H); 4.86 (d, 1H); 4.93 (d, 1H); 5.51 (t, 1H). Mass spectrum (chemical ionization, positive ions, ammonia): 790 ($M+NH_4^+$), 294

Working in a similar manner the following compound was prepared

3beta,14-di-(ethoxymethyl)-5beta,14beta-androst-16-en-17-yl-triflate (m.p. 76°–78° C.)

$^1$H-NMR (300 MHz, CDCl$_3$): delta (ppm): 0.93 (s, 3H); 1.07 (s, 3H); 1.17 (t, 3H); 1.20 (t, 3H); 1.00–2.00 (m, 17H); 2.57 (dd, 1H); 2.63 (dd, 1H); 3.60 (q, 2H); 3.50–3.80 (m, 2H); 3.92 (bs, 1H); 4.68 (d, 1H); 4.70 (s, 2H); 4.76 (d, 1H); 5.52 (bs, 1H).

EXAMPLE 2

3beta-[[16-deoxy-2,4-di-(ethoxymethyl)-3-O-methyl-alpha-L-glucopyranosyl]oxy]-14-ethoxymethoxy-17-(4-fluorophenyl)-5beta,14beta-androst-16-ene To a solution of 3beta-[[6-deoxy-2,4-di-(ethoxymethyl)-3-O-methyl-alpha-L-glucopyranosyl]oxy]-14-ethoxymethoxy-5beta, 14beta-androstan-16-en-17-yl-triflate (5.8 g; 7.5 mmoles), prepared as described in Example 1, in dry tetrahydrofuran (37 ml), PdCl$_2$[1,4-bis(diphenylphosphine)butane] (45 mg; 0.07 mmoles) and a solution circa 2M of 4-fluorophenylmagnesium bromide (7.5 ml; 15 mmoles) are added under nitrogen at room temperature.

The reaction mixture is then heated to reflux for 2 hours.

After cooling to room temperature, the mixture is diluted with ethyl ether (100 ml) and water (30 ml).

After acidification of the aqueous phase to pH 5–6 with 1N hydrochloric acid, the phases are separated, and the organic phase is extracted with ethyl ether ($3 \times 50$ ml).

The organic phases are combined and washed with an aqueous solution saturated with sodium bicarbonate, dried on sodium sulphate, shaked with animal charcoal and filtered.

Evaporation of the solvent leaves a crude product which is crystallized from an ethyl alcohol:water=8:2 mixture to yield a pure product (3.9 g) (m.p. 90°–92° C.).

$^1$H-NMR (300 MHz, CDCl$_3$): delta (ppm): 0.97 (s, 3H); 1.08 (s, 3H); 1.19 (t, 3H); 1.20 (t, 3H); 1.23 (t, 3H); 1.24 (d, 3H); 1.10–1.95 (m, 16H); 2.10 (dt, 1H); 2.53 (dd, 1H); 2.69 (dd, 1H); 3.13 (bt, 1H); 3.58 (s, 3H); 3.50–3.85 (m, 9H); 3.90 (bs, 1H); 4.60 (d, 1H); 4.72 (d, 1H); 4.76 (s, 2H); 4.80 (d, 1H); 4.87 (d, 1H); 4.93 (d, 1H); 5.70 (bs, 1H); 6.98 (t, 2H); 7.24 (dd, 2H). Mass spectrum (chemical ionization, positive ions, isobuthane): 643, 349

Working in a similar manner the following compounds were prepared 3-beta-[[6-deoxy-2,4-di-(ethoxymethyl)-3-O-methyl-alpha-glucopyransoyl]oxy]-14-ethoxymethoxy-17-(3-fluorophenyl)-5beta, 14beta-androst-16-ene (m.p. 93°–94° C.) $^1$H-NMR (300 MHz, CDCl$_3$): delta (ppm): 0.98 (s, 3H); 1.11 (s, 3H); 1.19 (t, 3H); 1.22 (t, 3H); 1.24 (t, 3H); 1.25 (d, 3H); 1.10–1.95 (m, 16H); 2.12 (dt, 1H); 2.55 (dd, 1H); 2.70 (dd, 1H); 3.13 (bt, 1H); 3.58 (s, 3H); 3.50–3.85 (m, 9H); 3.90 (bs, 1H); 4.61 (d, 1H); 4.72 (d, 1H); 4.76 (s, 2H); 4.80 (d, 1H); 4.88 (d, 1H); 4.93 (d, 1H); 5.79 (bs, 1H); 6.95 (td, 1H); 7.00 (dt, 1H); 7.08 (d, 1H); 7.25 (dd, 1H). Mass spectrum (chemical ionization, positive ions, ammonia): 736 (M+NH$_4^+$), 660, 349, 294

3beta-[[6-deoxy-2,4-di-(ethoxymethyl)-3-O-methyl-alpha-L-glucopyranosyl]oxy]-14-ethoxymethoxy)-17-(4-methoxyphenyl)-5beta, 14beta-androst-16-ene (m.p. 63°-65° C.) $^1$H-NMR (300 MHz, CDCl$_3$): delta (ppm): 0.97 (s, 3H); 1.10 (s, 3H); 1.18 (t, 3H); 1.20 (t, 3H); 1.23 (t, 3H); 1.24 (d, 3H); 1.05-1.95 (m, 16H); 2.12 (dt, 1H); 2.50 (dd, 1H); 2.68 (dd, 1H); 3.13 (bt, 1H); 3.58 (s, 3H); 3.50-3.80 (m, 9H); 3.80 (s, 3H); 3.90 (bs, 1H); 4.59 (d, 1H); 4.72 (d, 1H); 4.75 (s, 2H); 4.79 (d, 1H); 4.87 (d, 1H); 4.93 (d, 1H); 5.66 (bs, 1H); 6.83 (d, 2H); 7.23 (d, 2H). Mass spectrum (chemical ionization, positive ions, ammonia): 748 (M+NH$_4^+$), 655, 379, 294

3beta-[[6-deoxy-2,4-di-(ethoxymethyl)-3-O-methyl-alpha-L-glucopyransoyl]oxy]-4-ethoxymethyl-17-(3-methoxyphenyl)-5beta, 14beta-androst-16-ene (m.p. 84°-86° C.)

$^1$H-NMR (300 MHz, CDCl$_3$): delta (ppm): 0.98 (s, 3H); 1.12 (s, 3H); 1.19 (t, 3H); 1.21 (t, 3H); 1.23 (t, 3H); 1.24 (d, 3H); 1.10-1.95 (m, 16H); 2.15 (dt, 1H); 2.54 (dd, 1H); 2.70 (dd, 1H); 3.13 (bt, 1H); 3.58 (s, 3H); 3.50-3.80 (m, 9H); 3.81 (s, 3H); 3.91 (bs, 1H); 4.62 (d, 1H); 4.74 (d, 14H); 4.76 (s, 2H); 4.80 (d, 1H); 4.88 (d, 1H); 4.94 (d, 1H); 5.75 (bs, 1H); 6.80 (d, 1H); 6.85 (d, 1H); 6.90 (d, 1H); 7.22 (t, 1H). Mass spectrum (chemical ionization, positive ions, ammonia): 748 (M+NH$_4^+$)

3beta-[[6-deoxy-2,4-di-(ethoxymethyl)-3-O-methyl-alpha-L-glucopyransoyl] oxy]-14-ethoxymethoxy-17-phenyl-5beta,14beta-androst-16-ene (m.p. 80°-82° C.) $^1$H-NMR (300 MHz, CDCl$_3$): delta (ppm): 0.98 (s, 3H); 1.10 (s., 3H); 1.19 (t, 3H); 1.21 (t, 3H); 1.23 (t, 3H); 1.24 (d, 1.05-1.95 (m, 16H); 2.15 (dt, 1H); 2.57 (dd, 1H); 2.70 (dd, 1H); 3.13 (bt, 1H); 3.58 (s, 3H); 3.50-3.80 (m, 9H); 3.90 (bs, 1H); 4.61 (d, 1H); 4.74 (d, 1H); 4.76 (s, 2H); 4.79 (d, 1H); 4.88 (d, 1H); 4.93 (d, 1H); 5.74 (bs, 1H); 7.25 (m, 5H). Mass spectrum (chemical ionization, positive ions, ammonia): 719 (M+NH$_4^+$), 349, 331

3beta-[[6-deoxy-2,4-di-(ethoxymethyl-3-O-methyl-alpha-L-glucopyranosyl]oxy]-14-ethoxymethoxy-17-(4-trifluoromethylphenyl)5beta,14beta-androst-16-ene $^1$H-NMR (300 MHz, CDCl$_3$): delta (ppm): 0.98 (s, 3H); 1.11 (s, 3H); 1.19 (t, 3H); 1.20 (t, 3H); 1.24 (t, 3H); 1.25 (d, 3H); 1.10-2.00 (m, 16H); 2.13 (dt, 1H); 2.57 (dd, 1H); 2.72 (dd, 1H); 3.13 (bt, 1H); 3.58 (s, 3H); 3.50-3.80 (m, 9H); 3.90 (bs, 1H); 4.62 (d, 1H); 4.72 (d, 1H); 4.76 (s, 2H); 4.80 (d, 1H); 4.88 (d, 1H); 4.93 (d, 1H); 5.84 (bs, 1H); 7.40 (d, 2H); 7.55 (d, 2H). Mass spectrum (chemical ionization positive ions, ammonia): 786 (M+NH$_4^+$), 710, 294

3beta-[[6-deoxy-2,4-di-(ethoxymethyl)-3-O-methyl-alpha-L-glucopyransoyl]oxy]-14-ethoxymethoxy-17-(3-trifluoromethylphenyl)-5beta,14beta-androst-16-ene $^1$H-NMR (300 MHz, CDCl$_3$): delta (ppm): 0.98 (s, 3H); 1.11 (s, 3H); 1.19 (t, 3H); 1.21 (t, 3H); 1.23 (t, 3H); 1.24 (d, 3H); 1.00-1.95 (m, 16H); 2.12 (dt, 1H); 2.57 (dd, 1H); 2.71 (dd, 1H); 3.13 (bt, 1H); 3.58 (s, 3H); 3.50-3.85 (m, 9H); 3.90 (bs, 1H); 4.63 (d, 1H); 4.72 (d, 1H); 4.77 (s, 2H); 4.80 (d, 1H); 4.88 (d, 1H); 4.93 (d, 1H); 5.82 (bs, 1H); 7.35-7.55 (m, 4H). Mass spectrum (chemical ionization, positive ions, ammonia): 786 (M+NH$_4^+$), 710, 399, 294

3beta-[[6-deoxy-2,4-di-(ethoxymethyl )-3-O-methyl-alpha-L-glucopyranosyl]oxy]-14-ethoxymethoxy-17-(4-methylphenyl)-5beta, 14beta-androst-16-ene $^1$H-NMR (300 MHz, CDCl$_3$): delta (ppm): 0.98 (s, 3H); 1.10 (s, 3H); 1.19 (t, 3H); 1.21 (t, 3H); 1.23 (t, 3H); 1.24 (d, 3H); 1.00-2.00 (m, 16H); 2.15 (dt, 1H); 2.33 (s, 3H); 2.51 (dd, 1H); 2.69 (dd, 1H); 3.13 (bt, 1H); 3.58 (s, 3H); 3.50-3.80 (m, 9H); 3.90 (bs, 1H); 4.60 (d, 1H); 4.73 (d, 1H); 4.76 (s, 2H); 4.80 (d, 1H); 4.88 (d, 1H); 4.94 (d, 1H); 5.70 (bs, 1H); 7.11 (d, 2H); 7.20 (d, 2H). Mass spectrum (chemical ionization, positive ions, ammonia): 732 (M+NH$_4^+$), 639, 363, 294

3beta-[[6-deoxy-2,4-di-(ethoxymethyl-3-O-methyl-alpha-L-glucopyransoyl]oxy]-14-ethoxymethoxy-17-(3-methylphenyl)-5beta, 14beta-androst-16-ene (m.p. 83°-84° C.)

$^1$H-NMR (300 MHz, CDCl$_3$): delta (ppm): 0.98 (s, 3H); 1.10 (s,, 3H); 1.20 (t, 3H); 1.21 (t, 3H); 1.22 (t, 3H); 1.23 (d, 3H); 1.10-2.00 (m, 16H); 2.15 (d, 1H); 2.34 (s, 3H); 2.52 (dd, 1H); 2.70 (dd, 1H); 3.13 (bt, 1H); 3.58 (s, 3H); 3.50-3.80 (m, 9H); 3.90 (bs, 1H); 4.62 (d, 1H); 4.74 (d, 1H); 4.77 (s, 2H); 4.80 (d, 1H); 4.88 (d, 1H); 4.93 (d, 1H); 5.72 (bs, 1H); 7.10 (d, 3H); 7.19 (dd, 1H). Mass spectrum (chemical ionization, positive ions, ammonia): 732 (M+NH$_4^+$), 639, 363, 294

3beta-[[6-deoxy-2,4-di-(ethoxymethyl)-3-O-methyl-alpha-L-glucopyranosyl]oxy]-14-ethoxymethoxy-17-(2-naphthyl)-5beta-androst-16-ene (m.p. 101°-103° C.)

$^1$H-NMR (300 MHz, CDCl$_3$): delta (ppm): 1.00 (s, 3H); 1.19 (s, 3H); 1.22 (t, 3H); 1.24 (t, 3H); 1.25 (t, 3H); 1.26 (d, 3H); 1.60-2.00 (m, 16H); 2.28 (m, 1H); 2.60 (dd, 1H); 2.76 (bd, 1H); 3.14 (bt, 1H); 3.60 (s, 3H); 3.50-3.85 (m, 9H); 3.93 (bs, 1H); 4.68 (d, 1H); 4.78 (s, 2H); 4.81 (d, 1H); 4.82 (d, 1H); 4.90 (d, 1H); 4.95 (d, 1H); 5.89 (bs, 1H); 7.47 (m, 3H); 7.72-7.85 (m, 4H). Mass spectrum (chemical ionization, positive ions, ammonia): 768 (M+NH$_4^+$), 692, 675, 399, 381, 294

3beta-[[6-deoxy-2,4-di-(ethoxymethyl )-3-O-methyl-alpha-L-glucopyranosyl]oxy]-14-ethoxymethoxy-17-(3-fluoro-6-methylphenyl)-5beta,14beta-androst-16-ene (m.p. 85°-88° C.)

$^1$H-NMR (300 MHz, CDCl$_3$): delta (ppm): 0.98 (s, 3H); 0.99 (s, 3H); 1.21 (t, 3H); 1.23 (t, 3H); 1.24 (t, 3H); 1.25 (d, 3H); 1.00-2.00 (m, 17H); 2.23 (s, 3H); 2.63 (dd, 1H); 2.72 (bd, 1H); 3.14 (bt, 1H); 3.58 (s, 3H); 3.50-3.85 (m, 9H); 3.91 (bs, 1H); 4.77 (d, 1H); 4.78 (s, 2H); 4.80 (d, 1H); 4.89 (d, 1H); 4.92 (d, 1H); 4.95 (d, 1H); 5.53 (bs, 1H); 6.78 (dd, 1H); 6.86 (td, 1H); 7.13 (dd, 1H). Mass spectrum (chemical ionization, positive ions, ammonia): 750 (M+NH$_4^+$), 674, 658, 381, 365, 294

Working in a similar manner but starting from 3beta,14-di-(ethoxymethoxy)-5beta,14beta-androst-16-en-17-yl triflate, the following compounds were prepared 3beta,14-di-(ethoxymethoxy)-17-phenyl-5beta,14beta-androst-16-ene $^1$H-NMR (300 MHz, CDCl$_3$): delta (ppm): 0.97 (s, 3H); 1.11 (s, 3H); 1.19 (t, 3H); 1.22 (t, 3H); 1.00-2.00 (m, 16H); 2.15 (dt, 1H); 2.53 (dd, 1H); 2.71 (dd, 1H); 3.62 (q, 2H); 3.55-3.70 (m, 2H); 3.94 (bs, 1H); 4.62 (d, 1H); 4.73 (s, 2H); 4.75 (d, 1H); 5.76 (bs, I H); 7.30 (m, 5H).

3beta,14-di-(ethoxymethoxy)-17-(4-fluorophenyl)-5beta,4beta-androst-16-ene $^1$H-NMR (300 MHz, CDCl$_3$): delta (ppm): 0.98 (s, 3H); 1.09 (s, 3H); 1.20 (t, 3H); 1.22 (t, 3H); 1.00-2.00 (m, 16H); 2.10 (dt, 1H); 2.54 (dd, 1H); 2.70 (dd, 1H); 3.55-3.70 (m, 4H); 3.95 (bs, 1H); 4.62 (d, 1H); 4.72 (s, 3H); 4.74 (d, 1H); 5.71 (bs, 1H); 7.00 (t, 2H); 7.25 (dd, 2H). Mass spectrum (chemical ionization, positive ions, ammonia): 425 (M+1), 379, 349

EXAMPLE 3

3beta, 14-di-(ethoxymethoxy)-17-phenyl-5beta,14beta-androst-16-ene

To a solution of 3beta,14-di-(ethoxymethoxy)-5beta,14beta-androst-16-en-17-yl triflate (230 mg; 0.415 mmoles), prepared as described in Example 1, and palladium tetrakistriphenylphosphine (14 mg; 0.012 mmoles) in benzene (830 ul), an aqueous solution of 2M sodium carbonate (415 ul) and then a solution of phenylboronic acid (76 mg; 0.622 mmoles) in ethyl alcohol (210 ul) are added.

The reaction mixture is heated under reflux for 24 hours.

The suspension is then filtered, diluted with an aqueous solution saturated with sodium chloride (2 ml) and extracted with ethyl ether (3×20 ml).

The extracted organic phases are combined and dried on sodium sulphate.

After evaporation of the solvent under reduced pressure, the crude product is purified by column chromatography on silica gel (230–400 mesh) (eluent, hexane:ethyl acetate=95:5) to yield the desired product in the form of an oil (157 mg).

$^1$H-NMR (300 MHz, CDCl$_3$): delta (ppm): 0.97 (s, 3H); 1.11 (s, 3H); 1.19 (t, 3H); 1.22 (t, 3H); 1.00–2.00 (m, 16H); 2.15 (dt, 1H); 2.53 (dd, 1H); 2.71 (dd, 1H); 3.62 (q, 2H); 3.55–3.70 (m, 2H); 3.94 (bs, 1H); 4.62 (d, 1H); 4.73 (s, 2H); 4.75 (d, 1H); 5.76 (bs, 1H); 7.30 (m, 5H).

EXAMPLE 4

3beta-[[6-deoxy-2,4-di-(ethoxymethyl)-3-O-methyl-alpha-L-glucopyransoyl]oxy]-14-ethoxymethoxy-17beta-(4-trifluoromethyl-phenyl)-5beta,14beta-androstane To a solution of 3beta-[[6-deoxy-2,4-di-(ethoxymethyl)-3-O-methyl-alpha-L-glucopyranosyl]oxy]-14-ethoxymethoxy-17- (4-trifluoromethylphenyl)-5beta,1-4beta-androst-16-ene (3 g; 3.9 mmoles), prepared as described in Example 2, in ethyl acetate (39 ml), 10 % platinum-on-charcoal (1.5 g) is added, and the resultant suspension is hydrogenated at room temperature.

After filtering off the catalyst, the solvent is evaporated under reduced pressure.

The crude product thus obtained is purified by column chromatography on silica gel (230–400 mesh) (eluent, hexane: ethyl acetate=85:15) to yield the desired compound in the form of an oil (1.6 g).

$^1$H-NMR (300 MHz, CDCl$_3$): delta (ppm): 0.54 (s, 3H); 0.97 (s, 3H); 1.20 (t, 3H); 1.22 (t, 3H); 1.24 (t, 3H); 1.24 (d, 3H); 1.00–2.20 (m, 21H); 2.89 (m, 1H); 3.13 (bt, 1H); 3.57 (s, 3H); 3.50–3.80 (m, 9H); 3.90 bs, 1H); 4.60 (d, 1H); 4.76 (s, 2H); 4.80 (d, 1H); 4.86 (d, 1H); 4.87 (d, 1H); 4.93 (d, 1H); 7.42 (d, 2H); 7.49 (d, 2H). Mass spectrum (chemical ionization, positive ions, ammonia): 788 (M+NH$_4$+), 712, 294

Working in a similar manner the following compounds were prepared

3beta-[[6-deoxy-2,4-di-(ethoxymethyl)-3-O-methyl-alpha-L-glucopyranosyl]oxy]-14-ethoxymethoxy-17beta-(3-trifluoromethylphenyl)-5beta,14beta-androstane $^1$H-NMR (300 MHz, CDCl$_3$): delta (ppm): 0.51 (s, 3H); 0.97 (s, 3H); 1.20 (t, 3H); 1.22 (t, 6H); 1.23 (d, 3H); 1.10–2.30 (m, 21H); 2.88 (m, 1H); 3.13 (bt, 1H); 3.58 (s, 3H); 3.50–3.80 (m, 9H); 3.90 (bs, 1H); 4.57 (d, 1H); 4.76 (s, 2H); 4.80 (d, 1H); 4.87 (d, 1H); 4.88 (d, 1H); 4.93 (d, 1H); 7.33 (t, 1H); 7.40 (d, 1H); 7.45 (d, 1H); 7.64 (s, 1H). Mass spectrum (chemical ionization, positive ions, ammonia): 88 (M+NH$_4$+), 712, 401,294

3beta-[[6-deoxy-2,4-di-(ethoxymethyl)-3-methyl-alpha-L-glucopyransoyl]oxy]-14-ethoxymethoxy-17beta-(4-fluorophenyl)-5beta, 4beta-androstane $^1$H-NMR (300 MHz, CDCl$_3$): delta (ppm): 0.52 (s, 3H); 0.97 (s, 3H); 1.20 (t, 3H); 1.22 (t, 3H); 1.23 (t, 3H); 1.24 (d, 3H); 1.10–2.30 (m, 21H); 2.80 (m, 1H); 3.13 (bt, 1H); 3.57 (s, 3H); 3.50–3.80 (m, 9H); 3.90 (bs, 1H); 4.60 (d, 1H); 4.75 (s, 2H); 4.79 (d, 1H); 4.86 (d, 1H); 4.87 (d, 1H); 4.93 (d, 1H); 6.91 (t, 2H); 7.26 (dd, 2H). Mass spectrum (chemical ionization, positive ions, ammonia): 738 (M+NH$_4$+), 662, 294

3beta-[[6-deoxy-2,4-di-(ethoxymethyl)-3-O-methyl-alpha-L-glucopyranosyl]oxy]-14-ethoxymethoxy-17beta-(3-fluorophenyl)-5beta, 14beta-androstane $^1$H-NMR (300 MHz, CDCl$_3$): delta (ppm): 0.55 (s, 3H); 0.96 (s, 3H); 1.20 (t, 3H); 1.22 (t, 3H); 1.23 (t, 3H); 1.24 (d, 3H); 1.10–2.30 (m, 21H); 2.83 (m, 1H); 3.12 (bt, 1H); 3.57 (s, 3H); 3.50–3.80 (m, 9H); 3.89 (bs, 1H); 4.60 (d, 1H); 4.74 (s, 2H); 4.78 (d, 1H); 4.86 (d, 1H); 4.87 (d, 1H); 4.93 (d, 1H); 6.80–7.20 (m, 4H).

3beta-[[6-deoxy-2,4-di-(ethoxymethyl)-3-O-methyl-alpha-L-glucopyranosyl]oxy]-14-ethoxymethoxy-17beta-(4-methoxyphenyl)-5beta, 14beta-androstane $^1$H-NMR (300 MHz, CDCl$_3$): delta (ppm): 0.53 (s, 3H); 0.96 (s, 3H); 1.20 (t, 3H); 1.22. (t, 3H); 1.23 (t, 3H); 1.24 (d, 3H); 1.10–2.30 (m, 21H); 2.78 (m, 1H); 3.12 (bt, 1H); 3.57 (s, 3H); 3.50–3.80 (m, 9H); 3.79 (s, 3H); 4.61 (d, 1H); 4.76 (s, 2H); 4.79 (d, 1H); 4.86 (d, 1H); 4.87 (d, 1H); 4.93 (d, 1H); 6.79 (d, 2H); 7.21 (d, 2H). Mass spectrum (chemical ionization, positive ions, ammonia): 750 (M+NH$_4$+), 674, 363, 294

3beta-[[6-deoxy-2,4-di-(ethoxymethyl)-3-O-methyl-alpha-L-glucopyranosyl]oxy]-14-ethoxymethoxy-17beta-(3-methoxyphenyl)-5beta, 14beta-androstane $^1$H-NMR (300 MHz, CDCl$_3$): delta (ppm): 0.57 (s, 3H); 0.96 (s, 3H); 1.20 (t, 3H); 1.22 (t, 3H); 1.23 (t, 3H); 1.24 (d, 3H); 1.10–2.30 (m, 21H); 2.80 (m, 1H); 3.12 (bt, 1H); 3.57 (s, 3H); 3.50–3.80 (m, 9H); 3.80 (s, 3H); 4.63 (d, 1H); 4.76 (s, 2H); 4.79 (d, 1H); 4.86 (d, 1H); 4.87 (d, 1H); 4.93 (d, 1H); 6.70 (dd, 1H); 6.78 (s, 1H); 6.85 (d, 1H); 7.15 (t, 1H).

3beta-[[6-deoxy-2,4-di-(ethoxymethyl)-3-O-methyl-alpha-L-glucopyransoyl]oxy]-14-ethoxymethoxy-17beta-phenyl-5beta, 14beta-androstane $^1$H-NMR (300 MHz, CDCl$_3$): delta (ppm): 0.54 (s, 3H); 0.97 (s, 3H); 1.20 (t, 3H); 1.22 (t, 3H); 1.23 (t, 3H); 1.24 (d, 3H); 1.10–2.20 (m, 21H); 2.82 (t, 1H); 3.13 (bt, 1H); 3.57 (s, 3H); 3.50–3.80 (m, 9H); 3.90 (bs, 1H); 4.62 (d, 1H); 4.76 (s, 2H); 4.80 (d, 1H); 4.87 (d, 1H); 4.88 (d, 1H); 4.93 (d, 1H); 7.10–7.30 (m, 5H). Mass spectrum (chemical ionization, positive ions, ammonia): 721 (M+NH$_4$+)

3beta-[[6-deoxy-2,4-di-(ethoxymethyl)-3-O-methyl-alpha-glucopyranosyl]oxy]14-ethoxymethoxy-17beta-(4-methylphenyl)-5beta, 14beta-androstane $^1$ H-NMR (300 MHz, CDCl$_3$): delta (ppm): 0.54 (s, 3H); 0.96 (s, 3H); 1.20 (t, 3H); 1.22 (t, 3H); 1.23 (t, 3H); 1.24 (d, 3H); 1.10–2.20 (m, 21H); 2.31 (s, 3H); 2.80 (dd, 1H); 3.13 (bt, 1H); 3.58 (s, 3H); 3.50–3.80 (m, 9H); 3.90 (bs, 1H); 4.62 (d, 1H); 4.76 (s, 2H); 4.79 (d, 1H); 4.87 (d, 1H); 4.88 (d, 1H); 4.93 (d, 1H); 7.06 (d, 2H); 7.19 (d, 2H). Mass spectrum (chemical ionization, positive ions, ammonia): 734 (M+NH$_4$+), 658, 347, 294

3beta-[[6-deoxy-2,4-di-(ethoxymethyl)-3-O-methyl-alpha-L-glucopyranosyl]oxy]14-ethoxymethoxy-17beta-(3-methylphenyl)-5beta, 14beta-androstane ¹H-NMR (300 MHz, CDCl₃): delta (ppm): 0.53 (s, 3H); 0.96 (s, 3H); 1.20 (t, 3H); 1.22 (t, 3H); 1.23 (t, 3H); 1.24 (d, 3H); 1.10–2.20 (m, 21H); 2.32 (s, 3H); 2.80 (t, 1H); 3.13 (bt, 1H); 3.57 (s, 3H); 3.50–3.80 (m, 9H); 3.90 (bs, 1H); 4.60 (d, 1H); 4.75 (s, 2H); 4.79 (d, 1H); 4.86 (d, 1H); 4.87 (d, 1H); 4.93 (d, 1H); 6.97 (d, 1H); 7.05–7.15 (m, 3H). Mass spectrum (chemical ionization, positive ions, ammonia): 734 (M+NH₄⁺), 658, 348, 294

3beta,14-di-(ethoxymethoxy)-17beta-phenyl-5beta,1-4beta-androstane

¹H-NMR (300 MHz, CDCl₃): delta (ppm): 0.54 (s, 3H); 0.95 (s, 3H); 1.22 (t, 3H); 1.24 (t, 3H); 1.00–2.20 (m, 21H); 2.83 (t, 1H); 3.54 (m, 1H); 3.61 (q, 2H); 3.76 (m, 1H); 3.94 (bs, 1H); 4.63 (d, 1H); 4.72 (s, 2H); 4.88 (d, 1H); 7.15 (t, 1H); 7.20–7.35 (m, 4H).

3beta,14-di-(ethoxymethoxy)-17beta-(4-fluorophenyl)-5beta, 14beta-androstane

¹H-NMR (300 MHz, CDCl₃): delta (ppm): 0.53 (s, 3H); 0.97 (s, 3H); 1.22 (t, 3H); 1.25 (t, 3H); 1.00–2.30 (m, 21H); 2.81 (m, 1H); 3.54 (m, 1H); 3.63 (q, 2H); 3.76 (m, 1H); 3.95 (bs, 1H); 4.61 (d, 1H); 4.72 (s, 2H); 4.87 (d, 1H); 6.92 (t, 2H); 7.27 (dd, 2H). Mass spectrum (chemical ionization, positive ions, ammonia): 444, 427, 398, 381

3beta-[[6-deoxy-2,4-di-(ethoxymethyl)-3-O-methyl-alpha-L-glucopyranosyl]oxy]-14-ethoxymethoxy-17beta-(2-naphthyl)-5beta, 14beta-androstane ¹H-NMR (300 MHz, CDCl₃): delta (ppm): 0.57 (s, 3H); 0.98 (s, 3H); 1.22 (t, 3H); 1.24 (t, 3H); 1.25 (t, 3H); 1.26 (d, 3H); 1.00–2.30 (m, 21H); 3.02 (bt, 1H); 3.13 (bt, 1H); 3.59 (s, 3H); 3.50–3.85 (m, 9H); 3.92 (bs, 1H); 4.66 (d, 1H); 4.78 (s, 2H); 4.80 (d, 1H); 4.90 (d, 1H); 4.92 (d, 1H); 4.95 (d, 1H); 7.42 (m, 2H); 7.58 (d, 1H); 7.65–7.85 (m, 4H). Mass spectrum (chemical ionization, positive ions, ammonia): 770 (M+NH₄⁺), 694, 680, 405, 383, 294

3beta-[[6-deoxy-2,4-di-ethoxymethyl)-3-O-methyl-alpha-L-glucopyranosyl]oxy]-14-ethoxymethoxy-17beta-(3-fluoro-6-methylphenyl)-5beta, 14beta-androstane ¹H-NMR (300 MHz, CDCl₃): delta (ppm): 0.56 (s, 3H); 0.96 (s, 3H); 1.21 (t, 3H); 1.23 (t, 3H); 1.24 (d, 3H); 1.25 (t, 3H); 1.00–2.30 (m, 21H); 2.24 (s, 3H); 3.13 (bt, 1H); 3.20 (bt, 1H); 3.59 (s, 3H); 3.50–3.85 (m, 9H); 3.91 (bs, 1H); 4.64 (d, 1H); 4.77 (s, 2H); 4.80 (d, 1H); 4.88 (d, 1H); 4.91 (d, 1H); 4.94 (d, 1H); 6.73 (td, 1H); 7.01 (dd, 1H); 7.38 (dd, 1H). Mass spectrum (chemical ionization, positive ions, ammonia): 752 (M+NH₄⁺), 676, 441, 365, 294

EXAMPLE 5

3beta,14-di-(ethoxymethoxy)-17alpha-phenyl-5beta,1-4beta-androstane

To a solution of 3beta,14-di-(ethoxymethoxy)-17-phenyl-5beta,14beta-androst-17-ene (260 mg; 0.54 mmoles), prepared as described in Example 2 or 3, in ethyl alcohol (5.4 mL), 10% palladium-on-charcoal (14 mg) is added, and the resultant reaction mixture is hydrogenated at room temperature.

After filtering off the catalyst, the solvent is removed by evaporation under reduced pressure. The crude product thus obtained is purified by column chromatography on silica gel (230–400 mesh) (eluent, hexane:ethyl acetate=39:1) to yield the desired compound in the form of an oil (120 mg). ¹H-NMR (300 MHz, CDCl₃): delta (ppm): 0.90 (s, 3H); 0.93 (s, 3H); 1.21 (t, 3H); 1.22 (t, 3H); 0.90–2.20 (m, 21H); 3.18 (m, 1H); 3.62 (q, 2H); 3.60–3.70 (m, 1H); 3.80 (m, 1H); 3.94 (bs, 1H); 4.72 (s, 2H); 4.78 (d, 1H); 4.97 (d, 1H); 7.15–7.35 (m, 5H).

Working in a similar manner the following compound was prepared

3beta-[[6-deoxy-2,4-di-(ethoxymethyl)-3-O-methyl-alpha-L-glucopyranosyl]oxy]-14-ethoxymethyl-17-alfa-(4fluorophenyl)-5beta, 14beta-androstane ¹H-NMR (300 MHz, CDCl₃): delta (ppm): 0.88 (s, 3H); 0.94 (s, 3H); 1.22 (m, 12H); 2.05 (d, 2H); 0.80–2.20 (m, 19H); 3.12 (m, 2H); 3.57 (s, 3H); 3.50–3.80 (m, 9H); 3.90 (bs, 1H); 4.75 (s, 2H); 4.80 (d, 2H); 4.93 (d, 1H); 4.98 (d, 1H); 6.96 (t, 2H); 7.18 (dd, 2H).

EXAMPLE 6

3beta-[[6-deoxy-3-O-methyl-alpha-L-glucopyranosyl)oxy]-17beta-(4-trifluoromethylphenyl)-5beta,14beta-androstan-14-ol (Compound 1)

A solution of 3beta-[[6-deoxy-2,4-di-(ethoxymethyl)-3-O-methyl-alpha-L-glucopyranosyl]oxy]-14-ethoxymethoxy-17beta-(4-trifluoromethylphenyl)-5beta,1-4beta-androstane (1.6 g; 2.1 mmoles), prepared as described in Example 4, in tetrahydrofuran (21 ml), and a 10 % aqueous solution of hydrochloric acid (3.5 ml) are mixed and heated to 600° C. for 5 hours.

The reaction mixture is then poured into an aqueous solution saturated with sodium bicarbonate (30 ml) and extracted with methylene chloride (3×50 ml).

The organic phases are combined, dried on sodium sulphate and the solvent evaporated off under reduced pressure.

The crude product thus obtained is purified by column chromatography on silica gel (230–400 mesh) (eluent, hexane: ethyl acetate=1:1) and then crystallized from hexane: ethyl acetate=5:1 to give the desired compound (502 mg; m.p. 194°–195° C.).

¹H-NMR (300 MHz, CDCl₃): delta (ppm): 0.54 (s, 3H); 0.95 (s, 3H); 1.26 (d, 3H); 1.10–2.40 (m, 21H); 2.92 (m, 1H); 3.14 (td, 1H); 3.25 (t, 1H); 3.59 (m, 1H); 3.69 (s, 3H); 3.75 (qd, 1H); 3.99 (bs, 1H); 4.87 (d, 1H); 7.46 (d, 2H); 7.48 (d, 2H). Mass spectrum (chemical ionization, positive ions, ammonia): 596 (M+NH₄⁺), 418, 401, 178

Working in a similar manner the following compounds were prepared

3beta-[(6-deoxy-3-O-methyl-alpha-L-glucopyranosyl)oxy]-17beta-(3-trifluoromethylphenyl)-5beta,14beta-androstan-14-ol (Compound 2; m.p. 208°–209° C.)

¹H-NMR (300 MHz, CDCl₃): delta (ppm): 0.53 (s, 3H); 0.95 (s, 3H); 1.26 (d, 3H); 1.10–2.00 (m, 18H); 2.10 (m, 2H); 2.32 (m, 1H); 2.92 (m, 1H); 3.15 (td, 1H); 3.25 (t, 1H); 3.60 (m, 1H); 3.69 (s, 3H); 3.75 (qd, 1H); 3.99 (bs, 1H); 4.87 (d, 1H); 7.34 (t, 1H); 7.40 (d, 1H); 7.56 (d, 1H); 7.63 (s, 1H). Mass spectrum (chemical ionization, positive ions, ammonia): 596 (M+), 418, 401, 178

3beta-[(6-deoxy-3-O-methyl-alpha-L-glucopyranosyl)oxy]-17beta-(4-fluorophenyl)-5beta,14beta-androstan-14-ol (Compound 3; m.p. 125–130° C.)

¹H-NMR (300 MHz, CDCl₃): delta (ppm): 0.53 (s, 3H); 0.95 (s, 3H); 1.26 (d, 3H); 1.10–2.00 (m, 18H); 2.06 (m, 2H); 2.29 (m, 1H); 2.84 (m, 1H); 3.13 (td, 1H); 3.25 (t, 1H); 3.58 (m, 1H); 3.68 (s, 3H); 3.74 (qd, 1H); 3.98 (bs, 1H); 4.87 (d, 1H); 6.92 (t, 2H); 7.30 (dd, 2H). Mass spectrum (chemical ionization, positive ions, ammonia): 546 (M+), 369, 351, 178

3beta-[(6-deoxy-3-O-methyl-alpha-L-glucopyranosyl)oxy]-17alpha-(4-fluorophenyl)-5beta,1.4beta-androstan-14-ol (Compound 4; m.p. 202°–203° C.)

¹H-NMR (300 MHz, CDCl₃): delta (ppm): 0.83 (dt, 1H); 0.86 (s, 3H); 0.94 (s, 3H); 1.27 (d, 3H); 0.95–2.25 (m, 2OH); 3.13 (td, 1H); 3.25 (t, 1H); 3.37 (t, 1H); 3.58 (m, 1H); 3.68 (s, 3H); 3.75 (qd, 1H); 3.99 (bs, 1H); 4.86 (d, 1H); 6.97 (t, 2H); 7.18 (dd, 2H). Mass spectrum (chemical ionization, positive ions, ammonia): 546 (M+), 369, 351, 178

3beta-[(6-deoxy-3-O-methyl-alpha-L-glucopyranosyl)oxy]-17beta-(3-fluorophenyl)-5beta,14beta-androstan-14-ol (Compound 5; m.p. 153° C.)

¹H-NMR (300 MHz, CDCl3): delta (ppm): 0.57 (s, 3H); 0.96 (s, 3H); 1.27 (d, 3H); 1.10-2.00 (m, 18H); 2.07 (m, 2H); 2.18 (m, 1H); 2.86 (m, 1H); 3.14 (td, 1H); 3.25 (t, 1H); 3.59 (m, 1H); 3.69 (s, 3H); 3.75 (qd, 1H); 3.99 (bs, 1H); 4.87 (d, 1H); 6.83 (td, 1H); 7.05-7.25 (m, 3H). Mass spectrum (chemical ionization, positive ions, ammonia): 546 (M+), 368, 351, 178

3beta-[(6-deoxy-3-O-methyl-alpha-L-glucopyranosyl)oxy]-17beta-(4-methylphenyl)-5beta,14beta-androstan-14-ol (Compound 6; m.p. 150°-152° C.)

¹H-NMR (300 MHz, CDCl3): delta (ppm): 0.56 (s, 3H); 0.95 (s, 3H); 1.27 (d, 3H); 1.10-2.20 (m, 21H); 2.88 (m, 1H); 3.14 (td, 1H); 3.26 (t, 1H); 3.60 (m, 1H); 3.69 (s, 3H); 3.76 (qd, 1H); 3.99 (bs, 1H); 4.87 (d, 1H); 7.15 (t, 1H); 7.25 (t, 2H); 7.34 (d, 2H). Mass spectrum (chemical ionization, positive ions, ammonia): 558 (M+), 352, 333, 178

3beta-[(6-deoxy-3-O-methyl-alpha-L-glucopyranosyl)oxy]-17beta-(4-methoxyphenyl)-5beta,14-androstan-14ol (Compound 7; m.p. 178°-179° C.)

¹H-NMR (300 MHz, CDCl3): delta (ppm): 0.56 (s, 3H); 0.95 (s, 3H); 1.27 (d, 3H); 1.10-2.30 (m, 21H); 2.82 (dd, 1H); 3.14 (td, 1H); 3.26 (t, 1H); 3.58 (m, 1H); 3.69 (s, 3H); 3.75 (qd, 1H); 3.78 (s, 3H); 3.99 (bs, 1H); 4.87 (d, 1H); 6.80 (d, 2H); 7.25 (d, 2H). Mass spectrum (chemical ionization, positive ions, ammonia): 58 (M+), 381,363, 178

3beta-[(6-deoxy-3-O-methyl-alpha-L-glucopyranosyl)oxy]-17beta-(3-methoxyphenyl)-5beta,14beta-androstan-14ol (Compound 8; m.p. 153°-155° C.)

¹H-NMR (300 MHz, CDCl3): delta (ppm): 0.60 (s, 3H); 0.96 (s., 3H); 1.27 (d, 3H); 1.10-2.30 (m, 21H); 2.85 (1:1H); 3.15 (td, 1H); 3.26 (t, 1H); 3.60 (m, 1H); 3.69 (s, 3H); 3.75 (qd, 1H); 3.79 (s, 3H); 3.99 (bs, 1H); 4.87 (d, 1H); 6.71 (dd, 1H); 6,92 (d, 1H); 6.97 (d, 1H); 7,18 (t, 1H), Mass spectrum (chemical ionization, positive ions, ammonia): 558 (M+), 381, 363, 178

3beta-[(6-deoxy-3-O-methyl-alpha-L-glucopyranosyl)oxy]-17beta-(4-methylphenyl)-5beta,14beta-androstan-14-ol (Compound 9; m.p. 177°-178° C.)

¹H-NMR (300 MHz, CDCl3): delta (ppm): 0.56 (s, 3H); 0.95 (s, 3H); 1.26 (d, 3H); 1.10-2.30 (m, 21H); 2.31 (s, 3H); 2.83 (t, 1H); 3.14 (td, 1H); 3.26 (t, 1H); 3.60 (m, 1H); 3.69 (s, 3H); 3.76 (qd, 1H); 3.99 (bs, 1H); 4.87 (d, 1H); 7.06 (d, 2H); 7.22 (d, 2H). Mass spectrum (chemical ionization, positive ions, ammonia): 542 (M+), 365, 347

3beta-[(6-deoxy-3-O-methyl-alpha-L-glucopyranosyl)oxy]-17beta-(3-methylphenyl)-5beta,14beta-androstan-14-ol (Compound 10; m.p. 105°-110C.)

¹H-NMR (300 MHz, CDCl3): delta (ppm): 0.57 (s, 3H); 0.94 (s, 3H); 1.27 (d, 3H); 1.10-2.30 (m, 21H); 2.31 (s, 3H); 2.83 (t, 1H); 3.14 (td, 1H); 3.25 (t, 1H); 3.60 (m, 1H); 3.69 (s, 3H); 3.75 (qd, 1H); 3.99 (bs, 1H); 4.87 (d, 1H); 6.96 (m, 1H); 7.14 (m, 3H). Mass spectrum (chemical ionization, positive ions, ammonia): 542 (M+), 365, 348, 178

3beta-[(6-deoxy-3-O-methyl-alpha-L-glucopyranosyl)oxy]-17beta-(2-naphthyl)-5beta,14beta-androstan-14-ol (Compound 11; m.p. 178°-180° C.)

¹H-NMR (300 MHz, CDCl3): delta (ppm): 0.59 (s, 3H); 0.97 (s, 3H); 1.28 (d, 3H); 1.10-1.75 (m, 14H); 1.80-1.99 (m, 4H); 2.07-2.44 (m, 3H); 3.07 (t, 1H); 3.17 (td, 1H); 3.27 (t, 1H); 3.61 (m, 1H); 3.70 (s, 3H); 3.78 (qd, 1H); 4.00 (bs, 1H); 4.88 (d, 1H); 7.41 (m, 2H); 7.62 (d, 1H); 7.70-7.85 (m, 4H). Mass spectrum (chemical ionization, positive ions, ammonia): 578 (M+), 401,383, 178

3beta-[(6-deoxy-3-O-methyl-alpha-L-glucopyranosyl)oxy]-17beta(3-fluoro-6-methylphenyl)-5beta,14beta-androstan-14-ol (Compound 12; m.p. 212°-215° C.)

¹H-NMR (300 MHz, CDCl3): delta (ppm): 0.58 (s, 3H); 0.97 (s, 3H); 1.28 (d, 3H); 1.10-2.20 (m, 21H); 2.15 (s, 3H); 3.14 (td, 1H); 3.22 (t, 1H); 3.27 (t, 1H); 3.59 (m, 1H); 3.69 (s, 3H); 3.76 (qd, 1H); 4.00 (bs, 1H); 4.88 (d, 1H); 6.72 (td, 1H); 7.01 (dd, 1H); 7.42 (dd, 1H). Mass spectrum (chemical ionization, positive ions, ammonia): 560 (M+), 383, 365, 178

17beta-(4-fluorophenyl)-5beta,14beta-androstan-3beta,14-diol (Compound 13; m.p. 168°-171° C.)

¹H-NMR (300 MHz, CDCl3): delta (ppm): 0.54 (s, 3H); 0.95 (s, 3H); 1.10-2.20 (m, 2OH); 2.30 (m, 1H); 2.86 (m, 1H); 4.04 (bs, 1H); 6.93 (t, 2H); 7.30 (dd, 2H). Mass spectrum (chemical ionization, positive ions, ammonia): 386 (M+), 370, 351

Working in a similar way but starting from 3beta-](6-deoxy-2,4-di-(ethoxymethyl)-3-O-methyl-alpha-L-glucopyranosyl)oxy]-14-ethoxymethoxy-17-(4-fluorophenyl)-5beta, 14beta-androst-16-ene the following compound was prepared 3beta-[(6-deoxy-3-O-methyl-alpha-L- glucopyranosyl)oxy]-17-(4-fluorophenyl)-5beta,14beta-androst-16-en-14-ol (Compound 14; m.p. 180°-181C.)

¹H-NMR (300 MHz, CDCl3): delta (ppm): 1.00 (s, 3H); 1.11 (s, 3H); 1.26 (d, 3H); 1.10-2.00 (m, 16H); 2.09 (dt, 1H); 2.26 (dd, 1H); 2.75 (dd, 1H); 3.14 (td, 1H); 3.26 (t, 1H); 3.59 (m, 1H); 3.69 (s, 3H); 3.76 (qd, 1H); 3.98 (bs, 1H); 4.87 (d, 1H); 5.74 (t, 1H); 6.99 (t, 2H); 7.27 (dd, 2H). Mass spectrum (chemical ionization, positive ions, ammonia): 544 (M+), 527, 367, 349, 178

EXAMPLE 7

3beta-[[6-deoxy-di-(ethoxymethyl)-3-O-methyl-alpha-L-glucopyranosyl]oxy]-14ethoxymethoxy-17beta-phenyl-5beta,14beta-androstan-16alpha-ol Diborane is bubbled through a solution, at a temperature of 0° C., of 3beta-6-deoxy-2,4-di-(ethoxymethyl)-3-O-methyl-alpha-L-glucopyranosyl]oxy]-14-ethoxymethoxy-17-phenyl-5beta,14beta-androst-16-ene (1 g; 1.4 mmoles), prepared as described in Example 2, in dry tetrahydrofuran (29 ml) (diborane is prepared by dropwise addition of a solution of sodium boron hydride (750 mg; 20 mmoles) in diglyme (50 ml), in boron trifluoride etherate (3.58 ml; 28.5 mmoles), under nitrogen at room temperature).

The reaction mixture is then maintained under stirring overnight at room temperature.

After having carefully decomposed the diborane with an excess of water, there are added hydrogen peroxide (368 ul; 4.3 mmoles) and an aqueous solution of 2M sodium hydroxide up to pH 8-9 and the reaction mixture is maintained under stirring for 3 hours.

After dilution with ethyl ether and water, the phases are separated and the organic phase is washed with water and dried on sodium sulphate.

The solvent is then removed under reduced pressure.

The crude product thus obtained is purified by column chromatography on silica gel (230-400 mesh) (eluent, hexane: ethyl acetate=7:3) to give the desired compound in the form of an oil (720 mg).

1H-NMR (300 MHz, CDCl3): delta (ppm): 0.53 (s, 3H); 0.96 (s, 3H); 1.21 (t, 3H); 1.23 (t, 3H); 1.25 (t, 3H); 1.26 (d, 3H); 1.15–2.00 (m, 17H); 2.13 (dd, 1H); 2.36 (dd, 1H); 2.73 (d, 1H); 3.13 (t, 1H); 3.58 (s, 3H); 3.50–3.80 (m, 9H); 3.91 (bs, 1H); 4.68 (d, 1H); 4.77 (s, 2H); 4.80 (d, 1H); 4.81 (m, 1H); 4.87 (d, 1H); 4.91 (d, 1H); 4.94 (d, 1H); 7.27 (m, 5H). Mass spectrum (chemical ionization, positive ions, ammonia): 736 (M+NH4+), 692, 349, 294

EXAMPLE 8

3beta-[(6-deoxy-3-O-methyl-alpha-L-glucopyranosyl-)oxy]-17beta-phenyl-5beta,14beta-androstan-14,16alpha-diol (compound 15)

A solution of 3beta-[[6-deoxy-2,4-di-(ethoxymethyl)-3-O-methyl-alpha-L-glucopyranosyl]oxy]-14-ethoxymethoxy-17beta-phenyl-5beta,14beta-androstan-16alpha-ol (760 mg; 0.97 mmoles), prepared as described in Example 7, in tetrahydrofuran (12 ml), and an aqueous solution of 10% hydrochloric acid (1.4 ml) are mixed together and heated at 55° C. for 2 hours.

After dilution with ethyl ether (25 ml), the organic phase is washed with an aqueous solution of sodium bicarbonate and dried on sodium sulphate.

The solvent is then removed by evaporation under reduced pressure.

The crude product thus obtained is purified by column chromatography on silica gel (230–400 mesh) (eluent, methylene chloride:methyl alcohol=95:5) and crystallized from hexane:ethyl acetate=5:1 to give the desired compound (125 mg; m.p. 199°–2010° C.).

1H-NMR (300 MHz, CDCl3): delta (ppm): 0.54 (s, 3H); 0.94 (s, 3H); 1.28 (d, 3H); 1.10–2.00 (m, 17H); 2.16 (m, 2H); 2.77 (d, 1H); 3.14 (td, 1H); 3.26 (t, 1H); 3.60 (m, 1H); 3.69 (s, 3H); 3.76 (qd, 1H); 3.99 (bs, 1H); 4.82 (m, 1H); 4.87 (d, 1H); 7.15–7.35 (m, 5H). Mass spectrum (chemical ionization, positive ions, ammonia): 544 (M+), 384, 366, 349, 178.

EXAMPLE 9

Evaluation of the interaction with the alpha1 and alpha3 isoforms of rat (Na+ +K+)-ATPase The method of Noel F. et al., Biochemical Pharmacology, 40 (12), pp. 2611–2616, (1990) was used to evaluate the displacement of [3H]-ouabain in preparations of rat kidney and rat brain, containing various concentrations of the compounds of formula I of this invention, and digoxin as a reference compound.

The results, expressed as a percentage of the displacement of the [3H-ouabain from rat kidney (alpha1 isoform) and from rat brain (alpha3 isoform) and as K1(alpha3), for some representative compounds of formula I are shown in the following table.

TABLE 1

Percentage of displacement of [3H]-ouabain from preparations of rat kidney and brain and $K_1$ (alpha3) in the presence of compound 3, compound 5, compound 6, compound 7 and digoxin.

| | Percentage of displacement of [3H]-ouabain | | |
|---|---|---|---|
| | rat kidney $3 \times 10^{-6}$M (n = 3) | rat brain $10^{-6}$M (n = 3) | $K_1$ (alpha3) |
| Compound 3 | 7.5 ± 12.3 | 91.4 ± 0.5 | $31.0 \times 10^{-8}$M |
| Compound 5 | 13.9 ± 4.3 | 80.0 ± 1.4 | $13.7 \times 10^{-8}$M |
| Compound 6 | 13.4 ± 3.7 | 84.1 ± 0.8 | $9.8 \times 10^{-8}$M |
| Compound 7 | 3.3 ± 8.3 | 92.0 ± 1.3 | $18.0 \times 10^{-8}$M |

TABLE 1-continued

Percentage of displacement of [3H]-ouabain from preparations of rat kidney and brain and $K_1$ (alpha3) in the presence of compound 3, compound 5, compound 6, compound 7 and digoxin.

| | Percentage of displacement of [3H]-ouabain | | |
|---|---|---|---|
| | rat kidney $3 \times 10^{-6}$M (n = 3) | rat brain $10^{-6}$M (n = 3) | $K_1$ (alpha3) |
| Digoxin | 36 | 92 | $8.4 \times 10^{-8}$M |

These data show that the compounds of the present invention selectively interact with the high affinity sites (alpha3 isoform) significantly differentiating themselves from digoxin

We claim:

1. A compound of the formula I

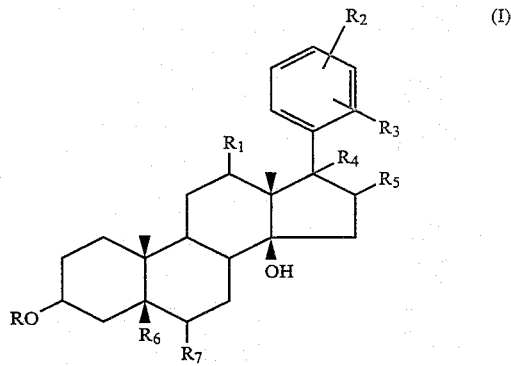

wherein

R is hydrogen, a glucosidic group or an aminoalkyl group of the formula —(CH2)n—NR8R9, wherein n is 2 or 3, and where R8 and R9, which may be the same or different, are straight or branched C1–C4 alkyl groups, or form, together with the nitrogen atom to which they are linked, a heterocycle having 5, 6 or 7 members, which may include one or two heteroatoms selected from the group consisting of oxygen and nitrogen, and may optionally be substituted with a straight or branched C1–C4 alkyl group;

R1 is hydrogen or hydroxy;

R2 and R3, which may be the same or different, are hydrogen, fluorine, chlorine, bromine, iodine, a straight or branched C1–C4 alkyl, a straight or branched C1–C4 polyhalogenated alkyl, OH, OR10, OCOR10, NH2, NHR10, N(R10)2, NHCOR10, SH, S(O)mR10, NHSO2R10, CHO, COOR10, CON(R10)2, or CN, where R10 is a straight or branched C1–C4 alkyl, a straight or branched C1–C4 polyhalogenated alkyl or an aryl and m is zero, 1 or 2; or R2 and R3 together form a C3–C4 alkylydene, which may have one or two unsaturated bonds, or they may form a —O—(CH2-)p—O—group, where p is 1 or 2;

R4 is hydrogen;

R5 is hydrogen or hydroxy;

or R4 and R5 together form a covalent bond; and R7 are hydrogen or together form a covalent bond; and the substituents in the 10-, 13-, and 14-position have beta configuration, provided, however, that when R, R1, R4, R5, R6 and R7 and either R₂ or R₃ are hydrogen atom, then the remaining of R₂ and R₃ is not a 3-methoxy group.

2. A compound according to claim 1, wherein $R_2$ and $R_3$, which may be the same or different, are hydrogen, fluorine, chlorine, bromine, iodine, methyl, ethyl, trifluoromethyl, OH, methoxy, CN, $NH_2$, $NHR_{10}$ or $N(R_{10})$ or $R_2$ and $R_3$ together form a $C_4$ alkylydene chain having one or two unsaturated bonds; and, $R_6$ and $R_7$ are hydrogen.

3. A compound according to claim 1, wherein $R_1$, $R_6$ and $R_7$ are hydrogen; $R_2$ and $R_3$, which may be the same or different, are hydrogen, fluorine, methyl, methoxy or trifluoromethyl, or $R_2$ and $R_3$ together form a $C_4$ alkylydene chain having two unsaturated bonds.

4. 3beta-[(6-deoxy-3-O-methyl-alpha-L-glucopyranosyl)oxy]-17beta-(4-fluorophenyl)-5beta, 14beta-androstan- 14-ol of claim 1.

5. 3beta-[(6-deoxy-3-O-methyl-alpha-L-glucopyranosyl)oxy]-17beta-(3-fluorophenyl)-beta, 14beta-androstan- 14-ol of claim 1.

6. 3beta-[(6-deoxy- 3-O-methyl-alpha-L-glucopyranosyl)oxy]-17beta-phenyl5beta,14beta-androstan-14-ol of claim 1.

7. 3beta-[(6-deoxy-3-O-methyl-alpha-L-glucopyranosyl)oxy]-17beta-(4-methoxyphenyl)-5beta,14beta-androstan-14-ol of claim 1.

8. 3beta-[(6-deoxy-3-O-methyl-alpha-L-glucopyranosyl)oxy]-17beta-(4-methylphenyl)-5beta,14beta-androstan-14-ol of claim 1.

9. 3beta-[[6-deoxy-3-O-methyl-alpha-L-glucopyranosyl]oxy]-17beta-(3,4-difluorophenyl)-5beta,14beta-androstan- 14-ol of claim 1.

10. 3beta-[[6-deoxy-3-O-methyl-alpha-L-glucopyranosyl]oxy]-17beta-(3-fluoro-2-methylphenyl)-5beta, 14beta-androstan-14-ol of claim 1.

11. 3beta-[[6-deoxy-3-O-methyl-alpha-L-glucopyranosyl]oxy]-17beta-(4-fluorophenyl)-5beta,1-4beta-androstan-14, 16alpha-diol of claim 1.

12. A pharmaceutical composition containing a therapeutically effective amount of a compound of the formula I

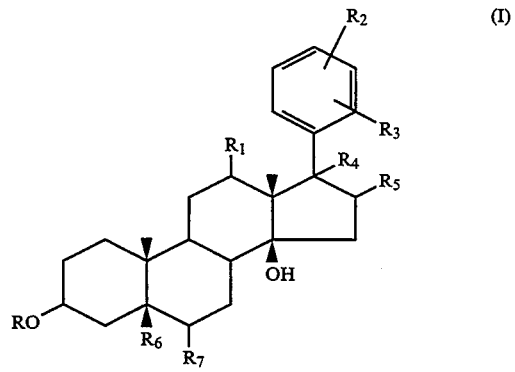

wherein
R is hydrogen, a glucosidic group or an aminoalkyl group of the formula $-(CH_2)_n-NR_8R_9$, wherein n is 2 or 3, and where $R_8$ and $R_9$, which may be the same or different, are straight or branched $C_1$-$C_4$ alkyl group,s or form, together with the nitrogen atom to which they are linked, a heterocycle having 5, 6 or 7 members, which may include one or two heteroatoms selected from the group consisting of oxygen and nitrogen, and may optionally be substituted with a straight or branched $C_1$-$C_4$ alkyl group; $R_1$ is hydrogen or hydroxy;

$R_2$ and $R_3$, which may be the same or different, are hydrogen, fluorine, chlorine, bromine, iodine, a straight or branched $C_1$-$C_4$ alkyl, a straight or branched $C_1$-$C_4$ polyhalogenated alkyl, OH, $OR_{10}$, $OCOR_{10}$, $NH_2$, $NHR_{10}$, $N(R_{10})_2$, $NHCOR_{10}$, SH, $S(O)_mR_{10}$, $NHSO_2R_{10}$, CHO, $COOR_{10}$, $CON(R_{10})_2$, or CN, where $R_{10}$ is a straight or branched $C_1$-$C_4$ alkyl, a straight or branched $C_1$-$C_4$ polyhalogenated alkyl or an aryl and m is zero, 1 or 2; or $R_2$ and $R_3$ together form a $C_3$-$C_4$ alkylydene, which may have one of: two unsaturated bonds, or they may form a $-O-(CH_2)_p-O-$ group, where p is 1 or 2;

$R_4$ is hydrogen;
$R_5$ is hydrogen or hydroxy;
or $R_4$ and $R_5$ together form a covalent bond;
$R_6$ and $R_7$ are hydrogen or together form a covalent bond; and the substituents in the 10-, 13-, and 14- position have beta configuration, provided, however, that when R, $R_1$, $R_4$, $R_5$, $R_6$ and $R_7$ and either $R_2$ or $R_3$ are hydrogen atom, then the remaining of $R_2$ and $R_3$ is lint a 3-methoxy group, and a pharmaceutically acceptable carrier.

* * * * *